US012614612B2

(12) United States Patent
Soon-Shiong et al.

(10) Patent No.: US 12,614,612 B2
(45) Date of Patent: *Apr. 28, 2026

(54) HLA TISSUE MATCHING AND METHODS THEREFOR

(71) Applicant: Nant Holdings IP, LLC, Culver City, CA (US)

(72) Inventors: Patrick Soon-Shiong, Culver City, CA (US); John Zachary Sanborn, Culver City, CA (US)

(73) Assignees: Nant Holdings IP, LLC, Culver City, CA (US); NantOmics, LLC, Culver City, CA (US)

( * ) Notice: Subject to any disclaimer, the term of this patent is extended or adjusted under 35 U.S.C. 154(b) by 279 days.

This patent is subject to a terminal disclaimer.

(21) Appl. No.: 18/434,510

(22) Filed: Feb. 6, 2024

(65) Prior Publication Data

US 2024/0177804 A1 May 30, 2024

Related U.S. Application Data

(60) Continuation of application No. 18/192,331, filed on Mar. 29, 2023, now Pat. No. 11,948,663, which is a (Continued)

(51) Int. Cl.
   *G16B 35/10*      (2019.01)
   *C12Q 1/6881*    (2018.01)
   (Continued)

(52) U.S. Cl.
   CPC ............. *G16B 35/10* (2019.02); *G16B 20/20* (2019.02); *G16B 30/10* (2019.02); *G16B 40/00* (2019.02); *G16B 50/30* (2019.02); *C12Q 1/6881* (2013.01)

(58) Field of Classification Search
   CPC ...... C12Q 1/6881; G16B 35/00; G16B 35/10; G16B 35/20; G16B 99/00; G16B 30/00;
   (Continued)

(56) References Cited

U.S. PATENT DOCUMENTS 5,468,611 A   11/1995   Baxter-Lowe et al.
11,646,103 B2   5/2023   Soon-Shiong et al.
(Continued)

FOREIGN PATENT DOCUMENTS

CN     104838269 A    8/2015
CN     105283557 A    1/2016
(Continued)

OTHER PUBLICATIONS

International Search Report and Written opinion received in PCT Application Serial No. PCT/US2018/049560 dated Mar. 27, 2019, 10 pages.
(Continued)

*Primary Examiner* — Jesse P Frumkin
(74) *Attorney, Agent, or Firm* — Umberg Zipser LLP; Martin Fessenmaier; Priti Phukan

(57) ABSTRACT

Contemplated systems and methods use high-accuracy in silico HLA analysis to so establish a transplant match database suitable for transplantation, and particularly stem cell and solid organ transplant.

18 Claims, 4 Drawing Sheets

Public dataset

| Sample | HLA | Prediction | Published | Prediction | Published |
|---|---|---|---|---|---|
| NA19238 | HLA-A | A*30:01:01 | A*30:01 | A*36:01 | A*36:01 |
| NA19238 | HLA-B | B*53:01:01 | B*53:01 | B*57:03:01 | B*57:03 |
| NA19238 | HLA-C | C*18:02 | C*18:01¹ | C*04:01:01 | C*04:01 |
| NA19238 | DRB1 | DRB1*16:02:01 | DRB1*16:02 | DRB1*11:01:02 | DRB1*11:01 |
| NA19238 | DQB1 | DQB1*06:02:01 | DQB1*06:02 | DQB1*05:02:01 | DQB1*05:02 |
| | | | | | |
| NA19239 | HLA-A | A*02:01:01 | A*02:01 | A*68:02:01 | A*68:02 |
| NA19239 | HLA-B | B*35:01:01 | B*35:01 | B*52:01:02 | B*52:01 |
| NA19239 | HLA-C | C*04:01:01 | C*04:01 | C*16:01:01 | C*16:01 |
| NA19239 | DRB1 | DRB1*13:01:01 | DRB1*13:01 | DRB1*12:01:01 | DRB1*13:01² |
| NA19239 | DQB1 | DQB1*05:01:01 | DQB1*05:01 | DQB1*03:01:01 | DQB1*03:01 |
| | | | | | |
| NA19240 | HLA-A | A*30:01:01 | A*30:01 | A*68:02:01 | A*68:02 |
| NA19240 | HLA-B | B*35:01:01 | B*35:01 | B*57:03:01 | B*57:03 |
| NA19240 | HLA-C | C*18:02 | C*18:01¹ | C*04:01:01 | C*04:01 |
| NA19240 | DRB1 | DRB1*16:02:01 | DRB1*16:02 | DRB1*12:01:01 | DRB1*12:01 |
| NA19240 | DQB1 | DQB1*05:02:01 | DQB1*05:02 | DQB1*03:01:01 | DQB1*03:01 |

Three discrepancies which can be explained as incorrect data in the published record. The HLA prediction method presented here has demonstrated 100% accuracy across a diverse panel of 5 HLAs in 3 individual datasets. ¹According to the data, there is no support for "Published" C*18:01, while there is lots of support for the Predicted C*18:02. ²Mendelian Inheritance dictates the "Published" DRB1*13:01 on both alleles is impossible

Related U.S. Application Data division of application No. 16/644,936, filed as application No. PCT/US2018/049560 on Sep. 5, 2018, now Pat. No. 11,646,103.

(60) Provisional application No. 62/554,655, filed on Sep. 6, 2017.

(51) Int. Cl.
| | |
|---|---|
| *G16B 20/20* | (2019.01) |
| *G16B 30/10* | (2019.01) |
| *G16B 40/00* | (2019.01) |
| *G16B 50/30* | (2019.01) |

(58) Field of Classification Search
CPC ........ G16B 30/10; G16B 30/20; G16B 20/00; G16B 20/10; G16B 20/20; G16B 20/30; G16B 20/40; G16B 20/50; G16B 50/00; G16B 50/10; G16B 50/20; G16B 50/30; G16B 50/40; G16B 50/50
See application file for complete search history.

(56) References Cited

U.S. PATENT DOCUMENTS

| | | | |
|---|---|---|---|
| 11,948,663 B2 * | 4/2024 | Soon-Shiong | ......... G16B 50/30 |
| 2013/0276154 A1 | 10/2013 | West | |
| 2016/0034666 A1 | 2/2016 | Hsu | |
| 2016/0125128 A1 | 5/2016 | Yang et al. | |
| 2018/0237949 A1 | 8/2018 | Sanborn | |
| 2020/0051666 A1 | 2/2020 | Smith et al. | |

FOREIGN PATENT DOCUMENTS

| | | | |
|---|---|---|---|
| CN | 111213210 A | 5/2020 | |
| WO | 2011138786 A2 | 11/2011 | |
| WO | 2017035392 A1 | 3/2017 | |
| WO | 2017139694 A1 | 8/2017 | |
| WO | 2019050958 A2 | 3/2019 | |
| WO | 2019050958 A3 | 5/2019 | |

OTHER PUBLICATIONS

Zhou et al., "Application of high-throughput, high-resolution and cost-effective next generation sequencing-based large-scale HLA typing in donor registry", Tissue Antigens, 2014, vol. 85, No. 1, 9 pages.

Boegel et al., "In Silico HLA Typing Using Standard RNA-Seq Sequence Reads", Molecular Typing of Blood Cell Antigens, Methods in Molecular Biology, 2015, vol. 1310, pp. 247-258.

Kawaguchi et al., "HLA-HD: An accurate HLA typing algorithm for next-generation sequencing data", Human Mutation, 2017, vol. 38, pp. 788-797.

Intenational Preliminary Report on Patentability received in PCT Application Serial No. PCT/US2018/049560 dated Mar. 19, 2020, 8 pages.

Examination Report No. 1 received for Australian Patent Application Serial No. 2018330415 dated Feb. 2, 2021, 4 pages.

Office Action received for Canadian Patent Application Serial No. 3074734 dated Apr. 15, 2021, 4 pages.

Extended European Search Report received for European Patent Application Serial No. 18854497.7 dated Apr. 30, 2021, 7 pages.

Weimer, Eric T., Maureen Montgomery, Rosanne Petraroia, John Crawford, and John L. Schmitz. "Performance characteristics and validation of next-generation sequencing for human leucocyte antigen typing." The Journal of Molecular Diagnostics 18, No. 5 (2016): 668-675. (Year: 2016).

Buchkovich, Martin. "GitHub—ExpressionAnalysis/HLAProfiler: Using k-nners to call HLA alleles in RNA sequencing data". In GitHub [online]. Jul. 18, 2017; [retrieved on May 20, 2022]. Retrieved from the Internet: <https://github.conn/ExpressionAnalysis/HLAProfiler > (Year: 2017).

Buchkovich, Martin. "Commits . ExpressionAnalysis/HLA Profiler • GitHub". In GitHub [online]. Jul. 18, 2017; [retrieved on May 20, 2022]. Retrieved from the Internet: <https://github.conn/ExpressionAnalysis/HLAProfiler/connnnits/nnaster> (Year: 2017).

De Bakker, Paul I W; Raychaudhuri, Soumya; de Bakker, Paul. Human Molecular Genetics 21: R29-R36. Oxford Univ Press. (Oct. 15, 2012) (Year: 2012).

Iqbal, Zamin; Caccamo, Mario; Turner, Isaac; Flicek, Paul; McVean, Gil. Nature Genetics 44.2: 226-32. New York: Nature Publishing Group. (Feb. 2012) (Year: 2012).

Gourraud, Pierre-Antoine; Khankhanian, Pouya; Cereb, Nezih; Yang, Soo Young; Feolo, Michael; et al. PLoS One 9.7: NA. Public Library of Science. (Jul. 2, 2014) (Year: 2014).

Dilthey, Alexander, et al. "Improved genome inference in the MHC using a population reference graph." Nature genetics 47.6 (2015) : 682-688. (Year: 2016).

First Office Action received for China Patent Application Serial No. 201880066387.7 dated Jan. 20, 2023, 14 pages (Including English Translation).

* cited by examiner

Public dataset

| Sample | HLA | Prediction | Published | Prediction | Published |
|---|---|---|---|---|---|
| NA19238 | HLA-A | A*30:01:01 | A*30:01 | A*36:01 | A*36:01 |
| NA19238 | HLA-B | B*53:01:01 | B*53:01 | B*57:03:01 | B*57:03 |
| NA19238 | HLA-C | C*18:02 | C*18:01[1] | C*04:01:01 | C*04:01 |
| NA19238 | DRB1 | DRB1*16:02:01 | DRB1*16:02 | DRB1*11:01:02 | DRB1*11:01 |
| NA19238 | DQB1 | DQB1*06:02:01 | DQB1*06:02 | DQB1*05:02:01 | DQB1*05:02 |
| | | | | | |
| NA19239 | HLA-A | A*02:01:01 | A*02:01 | A*68:02:01 | A*68:02 |
| NA19239 | HLA-B | B*35:01:01 | B*35:01 | B*52:01:02 | B*52:01 |
| NA19239 | HLA-C | C*04:01:01 | C*04:01 | C*16:01:01 | C*16:01 |
| NA19239 | DRB1 | DRB1*13:01:01 | DRB1*13:01 | DRB1*12:01:01 | DRB1*13:01[2] |
| NA19239 | DQB1 | DQB1*05:01:01 | DQB1*05:01 | DQB1*03:01:01 | DQB1*03:01 |
| | | | | | |
| NA19240 | HLA-A | A*30:01:01 | A*30:01 | A*68:02:01 | A*68:02 |
| NA19240 | HLA-B | B*35:01:01 | B*35:01 | B*57:03:01 | B*57:03 |
| NA19240 | HLA-C | C*18:02 | C*18:01[1] | C*04:01:01 | C*04:01 |
| NA19240 | DRB1 | DRB1*16:02:01 | DRB1*16:02 | DRB1*12:01:01 | DRB1*12:01 |
| NA19240 | DQB1 | DQB1*05:02:01 | DQB1*05:02 | DQB1*03:01:01 | DQB1*03:01 |

Three discrepancies which can be explained as incorrect data in the published record. The HLA prediction method presented here has demonstrated 100% accuracy across a diverse panel of 5 HLAs in 3 individual datasets. [1]According to the data, there is no support for "Published" C*18:01, while there is lots of support for the Predicted C*18:02. [2]Mendelian Inheritance dictates the "Published" DRB1*13:01 on both alleles is impossible

Fig. 1

Lab Patient Validation

| | HLA-A | | HLA-B | | HLA-C | | HLA-DRB1 | | HLA-DQB1 | | % Correct |
|---|---|---|---|---|---|---|---|---|---|---|---|
| Patient 1 | A*01:01:01 | A*31:01 | B*51:01 | B*57:01 | C*06:02 | C*15:02 | DRB1*01:01 | DRB1*07:01 | DQB1*03:03 | DQB1*05:01 | 100% |
| Patient 2 | A*24:02 | A*30:02 | B*18:01 | B*44:02 | C*05:01 | C*12:03 | DRB1*07:01 | DRB1*11:01 | DQB1*03:01 | DQB1*03:03 | 100% |
| Patient 3 | A*02:01 | A*03:01 | B*40:01 | B*40:01 | C*03:04 | C*03:04 | DRB1*04:04 | DRB1*15:01 | DQB1*03:02 | DQB1*06:02 | 100% |
| Patient 4 | A*02:01 | A*11:01 | B*44:03 | B*55:01 | C*03:03 | C*04:01 | DRB1*01:01 | DRB1*07:01 | DQB1*02:02 | DQB1*05:01 | 100% |
| Patient 5 | A*02:01 | A*02:01 | B*07:02 | B*15:01 | C*03:02 | C*07:01 | DRB1*01:01 | DRB1*04:01 | DQB1*03:02 | DQB1*05:01 | 100% |
| Patient 6 | A*02:01 | A*29:01 | B*14:02 | B*35:03 | C*04:01 | C*08:02 | DRB1*07:01 | DRB1*12:01 | DQB1*02:02 | DQB1*03:01 | 100% |
| Patient 7 | A*02:01 | A*68:01 | B*44:02 | B*44:03 | C*05:01 | C*16:01 | DRB1*04:01 | DRB1*07:01 | DQB1*02:02 | DQB1*03:01 | 100% |
| Patient 8 | A*01:01 | A*31:01 | B*08:01 | B*40:01 | C*03:02 | C*07:01 | DRB1*03:01 | DRB1*04:04 | DQB1*02:01 | DQB1*03:02 | 100% |
| Patient 9 | A*02:06 | A*33:01 | B*55:02 | B*39:01 / 06 | C*03:03 | C*07:01 | DRB1*14:03 | DRB1*15:02 | DQB1*03:01 | DQB1*05:01 | 100% |
| Patient 10 | A*01:01 | A*29:01 | B*07:02 | B*08:01 | C*07:01 | C*07:02 | DRB1*03:01 | DRB1*15:01 | DQB1*02:01 | DQB1*06:02 | 100% |
| Patient 11 | A*02:01 | A*03:01 | B*35:03 | B*35:03 | C*04:01 | C*12:03 | DRB1*11:01 | DRB1*12:01 | DQB1*03:01 | DQB1*03:01 | 100% |
| Patient 12 | A*01:01 | A*25:01 | B*08:01 | B*35:02 | C*04:01 | C*07:01 | DRB1*03:01 | DRB1*11:04 | DQB1*02:01 | DQB1*06:03 | 100% |
| Patient 13 | A*02:01 | A*24:02 | B*14:01 | B*44:02 | C*07:04 | C*08:02 | DRB1*07:01 | DRB1*11:01 | DQB1*02:02 | DQB1*03:01 | 100% |
| Patient 14 | A*26:01 | A*26:01 | B*35:02 | B*38:01 | C*04:01 | C*12:03 | DRB1*04:02 | DRB1*07:01 | DQB1*02:02 | DQB1*03:02 | 100% |
| Patient 15 | A*02:01 | A*25:01 | B*08:01 | B*35:03 | C*04:01 | C*07:01 | DRB1*11:04 | DRB1*12:03 | DQB1*03:01 | DQB1*03:01 | 100% |
| Patient 16 | A*03:02 | A*11:01 | B*35:08 | B*49:01 | C*04:01 | C*07:01 | DRB1*01:02 | DRB1*04:04 | DQB1*03:02 | DQB1*03:03 | 100% |
| Patient 17 | A*11:01 | A*68:01 | B*07:02 | B*44:02 | C*07:01 | C*07:04 | DRB1*01:01 | DRB1*15:01 | DQB1*05:01 | DQB1*06:02 | 100% |
| Patient 18 | A*26:01 | A*68:01 | B*13:01 | B*27:03 | C*02:02 | C*06:02 | DRB1*01:01 | DRB1*07:01 | DQB1*03:01 | DQB1*05:01 | 100% |
| Patient 19 | A*02:01 | A*26:01 | B*35:02 | B*38:01 | C*04:01 | C*12:03 | DRB1*11:04 | DRB1*11:04 | DQB1*03:01 | DQB1*03:01 | 100% |
| Patient 20 | A*03:01 | A*24:02 | B*18:01 | B*35:01 | C*04:01 | C*07:01 | DRB1*11:01 | DRB1*16:01 | DQB1*03:01 | DQB1*05:02 | 100% |

Fig. 2

| Patient | Pacbio HLA-A allele 1 | Pacbio HLA-A allele 2 | Predicted Allele 1 | Predicted Allele 2 |
|---|---|---|---|---|
| 891 260315 BC | A*01: | A*03: | *01:01 | *03:01 |
| 612 210814 BC | A*02: | A*11:01 | *02:07 | *11:01 |
| 665 220814 BC | A*02: | A*11: | *02:01 | *11:01 |
| 919 270215 BC | A*02: | A*11:01 | *02 | *11:01 |
| 948 080715 BC | A*02: | A*11: | *02:06 | *11:01 |
| 980 100215 BC | A*02: | A*11: | *02:03 | *11:01 |
| 1393 120216 BC | A*02: | A*11: | *02:06 | *11:01 |
| 618 080514 BC | A*02:01 | A*24:10 | *02:01 | *24:10 |
| 883 230115 BC | A*02:01 | A*11: | *02:01 | *11:01 |
| 936 060616 BC | A*02:01 | A*02:03 | *02:01 | *02:03 |
| 939 291215 BC | A*02:01 | A*33:03 | *02:01 | *33:03 |
| 1184 200815 BC | A*02:01 | A*11:02 | *02:01 | *11:02 |
| 1456 120416 BC | A*02:01 | A*02:03 | *02:01 | *02:03 |
| 1554 050716 BC | A*02:01 | A*11: | *02:01 | *11:01 |
| 1592.120816.B | A*02:01 | A*32:01 | *02:01 | *32:01 |
| 1632.220916.B | A*02:01 | A*02:06 | *02:01 | *02:06 |
| 269 080814 BC | A*02:03 | A*11:01 | *02:03 | *11:01 |
| 506 020114 BC | A*02:03 | A*02:07 | *02:03 | *02:07 |
| 834 090715 BC | A*02:03 | A*33: | *02:03 | *33:03 |
| 890 241014 N | A*02:03 | A*11:01 | *02:03 | *11:01 |
| 1054 170415 BC | A*02:03 | A*11:01 | *02:03 | *11:01 |
| 1066 041115 BC | A*02:03 | A*26:01 | *02:03 | *26:01 |
| 1171 070116 BC | A*02:03 | A*24:02 | *02:03 | *24:02 |
| 974 280815 BC | A*02:06 | A*11:01 | *02:06 | *11:01 |
| 047 271114 BC | A*02:07 | A*11:01 | *02:07 | *11:01 |
| 363 100714 BC | A*02:07 | A*33:03 | *02:07 | *33:03 |
| 742 081214 BC | A*02:07 | A*11:01 | *02:07 | *11:01 |
| 865 130815 BC | A*02:07 | A*26:01 | *02:07 | *26:01 |
| 973 270115 BC | A*02:07 | A*11:01 | *02:07 | *11:01 |
| 1030 220415 BC | A*02:07 | A*11:02 | *02:07 | *11:02 |
| 1128 110615 BC | A*02:07 | A*24:03 | *02:07 | *24:03 |
| 1145 230715 BC | A*02:07 | A*31:01 | *02:07 | *31:01 |
| 1165 050716 BC | A*02:07 | NA | *02:07 | *02:07 |
| 1176 191115 BC | A*02:07 | A*33:03 | *02:07 | *33:03 |
| 1277 290116 BC | A*02:07 | A*11:01 | *02:07 | *11:01 |
| 1323 031215 BC | A*02:07 | A*33:03 | *02:07 | *33:03 |
| 1324 070716 BC | A*02:07 | A*32:01 | *02:07 | *32:01 |
| 1341 050116 BC | A*02:07 | A*11:02 | *02:07 | *11:02 |
| 1419 040316 BC | A*02:07 | A*24:02 | *02:07 | *24:02 |
| 1538 300616 BC | A*02:07 | A*11:02 | *02:07 | *11:02 |

Fig. 3

| Patient | Pacbio HLA-A allele 1 | Pacbio HLA-A allele 2 | Predicted Allele 1 | Predicted Allele 2 |
|---|---|---|---|---|
| 490 040814 BC | A*03:01 | A*33:03 | *03:01 | *33:03 |
| 1604.041016.B | A*03:01 | A*24:02 | *03:01 | *24:02 |
| 420 121214 BC | A*11: | A*29: | *11:01 | *29:01 |
| 470 200415 BC | A*11: | NA | *11:01 | *11:02 |
| 765 061114 BC | A*11: | A*33:03 | *11:04 | *33:03 |
| 814 050814 BC | A*11: | A*24: | *11:01 | *24:02 |
| 786 261214 BC | A*11:01 | A*24:02 | *11:01 | *24:02 |
| 927 121015 BC | A*11:01 | A*24:02 | *11:01 | *24:02 |
| 958 260615 BC | A*11:01 | A*24:02 | *11:01 | *24:02 |
| 963 170616 BC | A*11:01 | A*24:02 | *11:01 | *24:02 |
| 1037 020415 BC | A*11:01 | A*24:02 | *11:01 | *24:02 |
| 1127 110615 BC | A*11:01 | A*24:02 | *11:01 | *24:02 |
| 1177 291015 BC | A*11:01 | A*24:02 | *11:01 | *24:02 |
| 1196 180815 BC | A*11:01 | A*33:03 | *11:01 | *33:03 |
| 1226 061115 BC | A*11:01 | NA | *11:01 | *11:01 |
| 1386 030316 BC | A*11:01 | A*33:03 | *11:01 | *33:03 |
| 1424 140416 BC | A*11:01 | A*32:01 | *11:01 | *32:01 |
| 1448 070416 BC | A*11:01 | A*33:03 | *11:01 | *33:03 |
| 1556 050716 BC | A*11:01 | A*33:03 | *11:01 | *33:03 |
| 1586 050816 BC | A*11:02 | A*33:03 | *11:02 | *33:03 |
| 1146 291015 BC | A*24: | A*33: | *24:02 | *33:03 |
| 153 220914 BC | A*24:02 | A*33:03 | *24:02 | *33:03 |
| 649 070414 BC | A*24:02 | A*30:01 | *24:02 | *30:01 |
| 1194 140815 BC | A*24:02 | A*33:03 | *24:02 | *33:03 |
| 1262 241115 BC | A*24:02 | A*33:03 | *24:02 | *33:03 |
| 1414 260516 BC | A*24:02 | NA | *24:02 | *24:02 |
| 609 170314 BC | A*24:07 | A*33:03 | *24:07 | *33:03 |
| 1602.290916.B | A*24:10 | A*34:01 | *24:10 | *34:01 |
| 1158 010616 BC | A*31:01 | A*33:03 | *31:01 | *33:03 |
| 785 101014 BC | A*33:03 | NA | *33:03 | *33:03 |
| 1539 300616 BC | A*02: | A*02:01 | *02:01 | *02:95 |
| 1470 220616 BC | A*02:01 | NA | *02:01 | *02 |
| 1409 310516 BC | A*11:01 | NA | *11:01 | *11 |
| 1255 030816 BC | A*02:01 | A*02:03 | *02:01 | *02:01 |
| 935 050215 BC | A*11:01 | NA | *11:01 | *11:12 |
| 1399 060516 BC | A*11:01 | NA | *11:01 | *11:155 |
| 106 040214 BC | A*24:02 | | *24:02 | *24:235 |
| 928 261114 N | A*01: | A*11:01 | *11:01 | *11:01 |
| 998 050315 BC | A*02:01 | A*23:01 | *02:01 | *11:02 |
| 1643.111016.B | A*03:01 | A*24:02 | *02:01 | *33:03 |

Fig. 4

HLA TISSUE MATCHING AND METHODS THEREFOR

This application is a continuation application of allowed US application with the Ser. No. 18/192,331, which was filed on Mar. 29, 2023, which claims priority to US application with the Ser. No. 16/644,936, which was filed Mar. 5, 2020, now U.S. Pat. No. 11,646,103, which is a 371 application of International patent application with the serial number PCT/US2018/049560, which was filed Sep. 5, 2018, and which claims priority to US Provisional application with the Ser. No. 62/554,655, which was filed Sep. 6, 2017.

FIELD OF THE INVENTION

The field of the invention is systems and methods for pre-transplant tissue matching, especially as it relates to in silico HLA determination.

BACKGROUND

The following description includes information that may be useful in understanding the present invention. It is not an admission that any of the information provided herein is prior art or relevant to the presently claimed invention, or that any publication specifically or implicitly referenced is prior art.

HLA typing remains critical in the practice of transplanting various solid organs and stem cells, and there are various systems and methods known in the art to determine the HLA type of a patient. Most commonly, HLA typing is performed using wet chemistry/serological methods or via nucleic acid analysis, and particularly sequencing or PCR-based methods. Such methods are in many cases satisfactory and will provide relatively accurate results. However, most common methods will require significant time and are often relatively expensive, especially where a large population is to be analyzed.

To address at least some of the drawbacks associated with the conventional methods, nested/tandem PCR can be employed, typically using raw blood samples as described in US 2011/0117553. In still other methods that are suitable for high throughput determination, as taught in US 2003/0165884, combined amplification and locus-specific capture probes are employed. Similarly, U.S. Pat. No. 7,917,297 describes various arrays of distinct capture nucleotides on a solid phase to enable rapid analysis. Unfortunately, such systems typically do not allow for highly accurate HLA determination as hybridization differences among HLA alleles are often only very minor. All publications and patent applications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

More recently, computer implemented methods were described that use, for example, exome sequencing data for determination of the HLA type as discussed in US 2016/0125128. In yet other examples, probabilistic analysis on sequence data is employed to determine the most likely HLA type as taught in US 2015/0110754, and WO 2017/035392 describes computer analysis using De Bruijn graphs. Notably, these methods are relatively fast, but have not been employed across larger sample populations.

Thus, even though there are various systems and methods for HLA typing known in the art, there is still a need to provide improved systems and implementations for HLA typing, and especially in silico HLA typing.

SUMMARY OF THE INVENTION

The inventive subject matter provides apparatus, systems, and methods in which HLA analysis is performed across a large population of samples to provide a bioinformatics database that assists in the identification of donor/recipient matches. For example, where bone marrow stem cell transplants are needed for liquid tumors, a complete and detailed HLA analysis of all bone marrow and cord blood donors is first established. This unique database can then serve as a bioinformatics universal engine for any recipient needing a bone marrow or cord blood donation. In another example, for solid organ transplantation, a complete a priori sequence analysis of all recipients waiting for a transplant is performed to determine the HLA type. Once a donor organ has become available, this database can become a universal match engine at the most granular HLA level, including minor and rare alleles. Thus, it should be appreciated that the systems and methods presented herein provide a rapid matching of donor and recipient at a highly accurate and comprehensive level across a large population of donors and/or recipients.

In one aspect of the inventive subject matter, the inventor contemplates a method of matching a donor tissue with a recipient tissue that includes a step of obtaining omics data for a plurality of donor samples, wherein each of the samples is a cord blood or bone marrow sample, and a further step of determining an HLA type for each of the donor samples using an in silico algorithm to so obtain a donor registry. In yet another step, the donor registry is used to identify one of the donor samples (e.g., cord blood) as being compatible with a recipient having a matching HLA type.

Likewise, in another aspect of the inventive subject matter, the inventor contemplates a method of matching a donor tissue with a recipient tissue that includes a step of obtaining omics data for a plurality of recipients, wherein each of the recipients is a solid organ recipient, and a further step of determining an HLA type for each of the recipients using an in silico algorithm to so obtain a recipient registry. In still another step, the recipient registry is used to identify one of the recipients as being compatible with a donor organ (e.g., lung, a liver, a heart, or skin) having a matching HLA type.

With respect to omics data for contemplated methods, exome sequencing data, whole genome sequencing data, and/or RNA sequencing data are especially preferred, and it is further preferred that the HLA type is determined to a depth of at least four digits. While not limiting to the inventive subject matter, the in silico algorithm uses a De Bruijn graph and a reference sequence. Most typically, the reference sequence includes alleles for at least one HLA type that have an allele frequency of at least 1%, at least ten different alleles for at least one HLA type, and/or includes alleles for at least two distinct HLA types. Thus, suitable HLA types will include one or more of an HLA-A type, an HLA-B type, an HLA-C type, a HLA-DRB-1 type, and a HLA-DQB-1 type.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWING

FIG. 1 is a table listing predicted and published HLA results for patient data from a public data set (1000 Genome project; subjects NA19238, NA19239, and NA19240).

FIG. 2 is a table listing in silico predicted and lab validated HLA results for actual patient data.

FIG. 3 is a table listing in silico predicted and HLA results obtained by long read sequencing for actual patient data.

FIG. 4 is a table listing in silico predicted and HLA results obtained by long read sequencing for actual patient data.

DETAILED DESCRIPTION

The inventor contemplates that a comprehensive in-depth bioinformatics universal HLA matching engine/database can be established in a conceptually simple and fast method that only requires omics data, either from a donor tissue or from a recipient waiting for a transplant. Indeed, it should be noted that omics data may be obtained from omics databases or sources that are intended for purposes other than HLA matching (e.g., for determination of likelihood for developing a disease, or family/ancestry determination) and that such databases and sources may use the omics data to generate additional value for the omics data provider. Viewed from a different perspective, it should be appreciated that the HLA type of a donor or recipient will be determined well in advance of a transplant event. Thus, even individuals without intent to donate cells or an organ at the time of omics data acquisition may now be identified and contacted as potential donors or recipients.

Therefore, the inventor generally contemplates use of various omics data to generate an HLA library that is suitable as a universal data hub for transplant donors and recipients. In this context, it must be recognized that omics data are currently ordered and obtained for a wide variety of reasons, medical and otherwise. The ever increasing quantity of such omics information can now serve as a broad spectrum source for HLA information. For example, omics data are ordered or generated to determine ancestry or ethnicity, for health assessment (e.g., to predict risk for a genetically linked disease), to identify and/or monitor a specific population such as felons, prison inmates, for population/ethnicity analysis in the context of epidemiology, and in the course of personalized treatment (e.g., cancer immune therapy).

Consequently, it should be noted that the type of omics data will vary considerably and will include whole genome sequencing, exome sequencing, transcriptome sequencing, and targeted sequencing. In this context, it should be recognized that current sequencing is almost exclusively purpose driven towards a specific goal (e.g., identification of somatic or germline mutations, diagnose a disease, determine ethnicity fractions, etc.). Contemplated systems and methods will advantageously allow repurposing omics data to identify an HLA type, which may be for the benefit of the individual that provided the omics data and/or for the benefit of another individual that has an HLA match with the individual. Of course, it is noted that the omics analysis may also be limited to a group of individuals that a priori intend to be a cell or tissue donor and/or to be a cell or tissue recipient. Therefore, exemplary donors will include bone marrow or stem cell donors, platelet donors, organ donors, while exemplary recipients include acute transplant recipients and individuals with an increased likelihood of organ insufficiency or failure (e.g., due to chronic progressive disease) or anticipated need for stem cell transplant (e.g., after bone marrow ablation).

There are numerous sources for omics data known in the art and all of the known sources are deemed suitable for use herein. For example, contemplated omics data especially include whole genome, exome sequencing, and/or transcriptome sequencing data from healthy or diseased tissue. In other aspects of the inventive subject matter, only partial omics data may be obtained. Among other options, such partial data will include data limited to chromosome 6, and especially location 6p21.3. Consequently, it should be noted that in silico analysis of omics data can be very flexible and indeed ingest data from DNA and RNA omics analyses (e.g., RNAseq data, exome sequencing, whole genome sequencing), or a combination of both DNA and RNA, to make the HLA predictions. Moreover, in silico analysis as presented in more detail below is highly accurate, and is very fast with run times typically less than 5 minutes to obtain a prediction on all 26 HLA types. Still further, new HLA alleles can be trivially added to the set of reference HLAs to predict on as is also noted in more detail below. Finally, it should be appreciated that contemplated systems and methods generally do not require population-based heuristics to produce accurate results.

With respect to determination of the HLA type for potential transplant donors it should be noted that the determination can be performed with or without intent of the donor to donate tissue to a third party with HLA match at the time the donor is tested. While some individuals may always wish to be available as a donor, others may consider such availability only months or even years after initial determination. For example, some donors may store cord blood tissue of their children for potential use in regenerative medicine practiced on the children, the children may at some point determine that their tissue (or HLA type information) may be used to assist in matching with a recipient having the same or a compatible HLA type. In another example, an individual will subscribe to a sequencing service that determines the genome, exome, and/or transcriptome of an individual for a purpose other than HLA determination (e.g., paternity analysis, SNP analysis, disease risk predisposition, family planning, personalized medicine, personalized fitness, personalized nutrition, etc.). For example, sequencing services (Otogenetics, Dante Labs, 23andme, Ancestry, MyHeritage, FamilyTreeDNA, etc.). Such services may provide as an additional incentive HLA determination to so allow a subscriber be notified where one or more other individuals with matching or compatible HLA type are identified. Therefore, particularly suitable sources for omics data include clinical services (i.e., for purpose of treatment of a disease) and non-clinical commercial services (i.e., for purpose other than treatment of a disease) that sequence the genome, exome, and/or transcriptome.

In still other embodiments, a blood or other organ bank may perform omics analyses on the banked tissue, possibly along with an identification of the tissue donor. In such case, the blood or organ/tissue bank may also represent an HLA repository or HLA data source that can be contacted to determine one or more HLA matches or HLA compatibility. Likewise, where a healthcare system (governmental or private) or insurance agency determines, stores, and/or has access to omics data of the members or subscribers, such omics data may be readily analyzed for determination of the HLA type. Therefore, it should be appreciated that the ever-increasing quantities of comprehensive omics data may be used as a secondary source of HLA data that can be determined without the need for a medical procedure or the need to contact the individual for whom the HLA type is to be determined.

Similarly, with respect to the determination of the HLA type for potential transplant recipients it is contemplated that the potential recipients need not be in an acute or even anticipated need for a transplant. Indeed, any person may develop the need for a transplant, either as a consequence of lifestyle, disease, and/or treatment. For example, various lifestyle options (e.g., drug use, excessive western diet, etc) will come along with an increased risk of organ failure, while diseases such as hepatitis, chronic kidney disease, diabetes, etc, will have an increased rate of developing organ insufficiency/failure. On the other hand, certain cancer treatments (and especially conventional chemotherapy) may result in organ damage such as bone marrow dysfunction. In still other examples, progress in regenerative medicine holds the promise of artificial organs from stem and/or progenitor cells. As such cells will typically not be drawn from the recipient, HLA matching is of paramount importance to avoid tissue rejection. Therefore, recipients need not be tested only when the need for transplantation arises, but HLA testing may be performed preemptively. For example, HLA testing may be performed as an optional preemptive service, or upon visit to a physician or clinic (typically necessitated by signs and symptoms of a disease). Most typically, such visits may be in connection with a condition that can escalate to organ insufficiency or organ failure, or with a condition that will ultimately require transplantation. Similarly, the condition may require a treatment that damages or kills an organ or tissue, such as chemotherapy and/or bone marrow ablation.

Thus, it should be appreciated that contemplated methods for determination of HLA type may originate from numerous tissues (healthy or diseased), especially including cord blood, whole blood, stem cells, buccal swabs, etc. Indeed, all donor tissues are deemed suitable for use herein. Therefore, suitable donor tissues include fresh liquid tissues (e.g., bone marrow aspirate, isolated stem cells), fresh solid tissues (e.g., skin tissue, cornea, kidney, lung, heart, etc.), and even preserved or cultured liquid tissues (e.g., frozen tissue sections, FFPE material, NK cells, T-cells, optionally genetically engineered and/or cultured or cryopreserved). Moreover, it is contemplated that the HLA analysis need not be performed on the donor tissue, but may also be performed on a donor that has consented to donate one or more tissues and/or organs upon finding a HLA compatible recipient or upon death. Thus, a match database may be expanded to also include potential donors.

For example, where a bone marrow stem cell transplant is needed in the course of treatment for a liquid tumor, a complete and detailed HLA record of bone marrow and/or cord blood donors in a HLA database can be queried. As noted above, such database can serve as a bioinformatics universal engine for any recipient needing a bone marrow or cord blood donation. In another example (e.g., in solid organ transplantation), a complete a priori sequence analysis of all recipients waiting for a transplant can be performed to determine the recipients' HLA type. Such information can then be deposited in a database. Once a donor organ has become available, the database can become a universal match engine at the most granular HLA level, including minor and rare alleles.

As will be readily appreciated the HLA database may be informationally coupled to a sequencing facility, an sequence analysis facility, a clinic, a (cord)blood bank, a (stem) cell bank, and/or a transplant clinic, etc., or may be distributed across multiple computers. For example, the HLA database may be centrally located in a service center that queries omics databases to receive omics data, or that initiates remote omics analysis on a computer that is informationally coupled to the omics database. Similarly, HLA analysis may also be done in the sequencing facility, sequence analysis facility, clinic, (cord)blood bank, (stem) cell bank, and/or transplant clinic, and results may be reported to the HLA database.

In this context it should be noted that any language directed to a computer should be read to include any suitable combination of computing devices, including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

For example, it is contemplated that tissue and organ donor samples can be tested for the HLA type using omics data as further described below, and such testing can be performed at the time of sample or organ acquisition. Alternatively, and especially where a donor has already undergone genetic testing (e.g., whole genome sequencing, exome sequencing, etc.), the omics information may also be drawn from a database already storing such data. Consequently, it should be appreciated that the point of tissue or organ acquisition may be different from the point of analysis. For example, where the tissue is cord blood, bone marrow, or stem cells, omics testing can be performed directly on a portion of the tissue. On the other hand, where the organ is a solid organ, testing can be done on a sample from the organ or on blood of the donor. On the other hand, where a recipient awaits a tissue or an organ transplant, the recipient can be tested for HLA type as discussed below, and the HLA information can be stored at a database. Therefore, it is noted that the location of HLA testing/analysis and tissue or organ collection can be the same or at different places. Consequently, HLA matching requests can be submitted from various locations, such as clinics, physician's offices, labs, oncology groups, commercial sequencing entities, which may be physically or informationally collocated with sequencing centers and/or HLA analysis services.

In still further contemplated aspects, the HLA analysis may be offered as an ancillary service to sequencing or omics processing centers to so provide an additional revenue stream. In such case, the HLA database may be a central registry that can be accessed by one or more parties as a function of particular credentials (e.g., member of organization, subscriber level, access privilege, etc.). Furthermore, it is contemplated that such central registry may use the entire genome information of the recipient and/or donor tissue, or may use only limited omics information, typically sequence information relevant to HLA location (chromosome 6p21.3).

Consequently, HLA matches may be identified at any one or more locations such as the sequencing facility, oncology group, clinic, physician's office, sequence analysis facility, (cord)blood bank, (stem) cell bank, transplant clinic, and/or the HLA database. HLA matches will typically be considered a match or a related HLA type where at least one, or at least two, or at least three, or at least four, or at least five, or at least six of the HLA alleles has an identity of at least two, more typically at least four, and most typically at least six digits. Typical examples for HLA alleles include HLA types will include one or more of an HLA-A allele, an HLA-B allele, an HLA-C allele, a HLA-DRB-1 allele, and a HLA-DQB-1 allele, each having a specific type.

While HLA types can be determined in numerous manners, all or almost all of them require significant time and equipment. Moreover, even where targeted HLA determination using allele specific PCR reactions is performed, accuracy is often less than desirable due to very small differences in base composition and melting point. Therefore, many conventional HLA typing methods will not resolve the HLA type to more than two or four digits. In addition, conventional HLA typing methods are in practice often not equipped to test for rare HLA types and as such tend to limit matching capability. Still further, conventional HLA tests are only performed for the purpose of imminent transplant with respect to a transplant recipient. Likewise, HLA tests are typically performed for most donors where donors have consented or otherwise already considered tissue donation (to themselves or others). To address these difficulties, the inventor now contemplates that an HLA database can be created using available omics data from any individual regardless of status (i.e., whether the specific individual is a donor or recipient, or whether the individual has considered or consented to cell or organ donation). As such, a universal HLA database can be created with significantly larger donor and recipient scope.

Most advantageously, existing omics data such as whole genome, exome, and/or transcriptome sequence data will be processed in an analysis module in which the omics sequences from individuals are processed using de Bruijn graph-based methods in conjunction with a synthetic reference sequence that includes known sequence information for a large variety of HLA allele sequences (e.g., HLA-A allele sequences, HLA-B allele sequences, HLA-C allele sequences, HLA-DRB-1 allele sequences, and HLA-DQB-1 allele sequences) to so obtain highly accurate alignments of various closely related sequences. It should be appreciated that such analysis is particularly advantageous for HLA determination from DNA and/or RNA sequencing information since each HLA-type has numerous often very similar alleles, and as traditional alignment methods often fail to have significant differentiation capabilities where sequences have high degree of similarity.

Indeed, HLA allele identification is among the most complex analytical problem in molecular diagnostics. First, more than 1300 alleles are now known to be present in worldwide populations at 12 expressed Class I and II loci. Moreover, the encoded polypeptides of these alleles differ from each other by one or more amino acid substitutions, resulting in substantial polymorphism. For example, the HLA-B locus has more than 400 known alleles. Second, new alleles are continuously added to the known sequences, rendering standard schemes quickly obsolete. Third, clinical laboratories are often asked to provide allele identification at various levels of resolution for different clinical situations (e.g., high resolution allele level typing is required for unrelated bone marrow transplantation while serological or low resolution typing is adequate for renal transplantation). Confounding all of these difficulties is the fact that an individual has alleles from both maternal and paternal origin, and that differences among alleles are often only very minor (e.g., change in a single, two, three of four amino acids). Table 1 below exemplarily illustrates the large diversity of HLA alleles.

TABLE 1

| Genetic locus | Allele Type | Number of known alleles |
|---|---|---|
| HLA-A | A1 to A80 | 214 |
| HLA-B | B7 to B81 | 425 |
| HLA-C | Cw1 to Cw10 | 108 |
| DRA | DR1 to DR18 | 2 |
| DRB1 | | 289 |
| DQA1 | DQ1 to DQ9 | 21 |
| DQB1 | | 46 |
| DPA1 | DPw1 to DPw6 | 19 |
| DPB1 | | 94 |

Therefore, error frequencies for hybridization-based methods such as sequence specific oligonucleotide probe hybridization or sequence specific primer PCR will be relatively high. Similarly, while direct sequencing of PCR products will remove difficulties associated with hybridization, analysis of the sequence reads is still time consuming, especially where a large group of samples must be processed/In this context, it should be noted that the systems and methods presented herein improve overall speed and accuracy, as well as the computer function as structuring and ranking of de Bruijn graph elements (and weighting) vastly increases accuracy and speed as compared to traditional data formats and processing schemes (e.g., multi-sequence alignment algorithms). Furthermore, it must be appreciated that the problem solved by the inventor is specific to the field of bioinformatics and would not even exist without computing of omics information. Finally, it should be recognized that the tasks performed by the analysis engine cannot be reasonably performed within the lifetime of a human without aid of computer systems.

In a typical example, a relatively large number of patient sequence reads mapping to chromosome 6p21.3 (or any other location near/at which HLA alleles are found) is provided by an omics database (e.g., from a clinic, oncology group, commercial genome analysis company, etc.) or sequencing facility or machine. Most typically, the sequence reads will be produced via NextGen sequencing (e.g., Illumina Solexa, Roche 454 sequencer, Ion Torrent sequencer, etc.) have a length of about 100-300 bases and comprise metadata, including read quality, alignment information, orientation, location, etc. Suitable formats include SAM, BAM, FASTA, GAR, etc., and it is generally preferred that the patient sequence reads provide a depth of coverage of at least 5×, more typically at least 10×, even more typically at least 20×, and most typically at least 30×. In addition to the patient sequence reads, contemplated methods further employ one or more reference sequences that include a plurality of sequences of known and distinct HLA alleles.

For example, a typical reference sequence may be a synthetic (without corresponding human or other mammalian counterpart) sequence that includes sequence segments of at least one HLA-type with multiple HLA-alleles of that HLA-type. For example, suitable reference sequences include a collection of known genomic sequences for at least 50 different alleles of HLA-A. Alternatively, or additionally, the reference sequence may also include a collection of known RNA sequences for at least 50 different alleles of HLA-A. Of course, and as further discussed in more detail below, the reference sequence is not limited to 50 alleles of HLA-A, but may have alternative composition with respect to HLA-type and number/composition of alleles. HLA Types will typically be expressed in conventional format. For example, an HLA type for a particular HLA gene may be notated as HLA-A*24:02:01:02L, where the first letter denotes the HLA gene, where 24:02 denotes type and sub-type, where:01 denotes a synonymous substitution, and where 02 denotes a substitution in a non-coding region. The last letter will denote protein expression. Suitable HLA allele sequences for the synthetic reference include all known sequences and can be accessed from IPD-IMGT/HLA (URL: cbi.ac.uk/ipd/imgt/hla/).

Most typically, the reference sequence will be in a computer readable format and will be provided from a database or other data storage device. For example, suitable reference sequence formats include FASTA, FASTQ, EMBL, GCG, or GenBank format, and may be directly obtained or built from data of a public data repository (e.g., IMGT, the International ImMunoGeneTics information system, or The Allele Frequency Net Database, EUROSTAM, www.allelefrequencies.net). Alternatively, the reference sequence may also be built from individual known HLA-alleles based on one or more predetermined criteria such as allele frequency, ethnic allele distribution, common or rare allele types, etc.

Using the reference sequence, the patient sequence reads can now be threaded through a de Bruijn graph to identify the alleles with the best fit as is also described in WO 2017/035392 (and its US national phase equivalent). In this context, it should be noted that each individual carries two alleles for each HLA-type, and that these alleles may be very similar, or in some cases even identical. Such high degree of similarity poses a significant problem for traditional alignment schemes. The inventor has now discovered that the HLA alleles, and even very closely related alleles can be resolved using an approach in which the de Bruijn graph is constructed by decomposing a sequence read into relatively small k-mers (typically having a length of between 10-20 bases), and by implementing a weighted vote process in which each patient sequence read provides a vote ("quantitative read support") for each of the alleles on the basis of k-mers of that sequence read that match the sequence of the allele. The cumulatively highest vote for an allele then indicates the most likely predicted HLA allele. In addition, it is generally preferred that each fragment that is a match to the allele is also used to calculate the overall coverage and depth of coverage for that allele as is also shown in more detail below.

For identification of the second allele for the same HLA-type, the inventor discovered that even relatively similar second alleles can be resolved in a more heuristic approach where the top-ranking HLA-allele is removed from further consideration, and where the remaining alleles are re-ranked using an adjusted ("scaled") vote. More specifically, the re-ranking is performed such that the vote value for k-mers that had a match with the top-ranking allele is reduced in the re-ranked vote. Such adjusted voting reduces (but not eliminates) the weighted votes for genotypes that are similar to the top-ranking allele, and thus give genetically less related alleles more weight. At the same time, similar alleles are not ignored. Ranking can be further refined by taking into consideration overall coverage and depth of coverage. For example, a first re-ranked allele may score higher with substantially lower overall coverage and depth of coverage than a second re-ranked allele. In such case, the second re-ranked allele may be more likely the correct allele. The top-ranking re-ranked allele is then the second allele for the same HLA-type. Of course, and as noted above, re-ranking may factor in overall coverage and depth of coverage, and may even lead to disqualification of an allele where the overall coverage and/or depth of coverage falls below a user defined threshold (e.g., overall coverage less than 94%, and/or depth of coverage less than 10×). In addition, using matching k-mers as a vote also allows identification of unique k-mers in a particular vote, which may serve as further guidance whether or not the particular vote is likely a correct prediction.

Of course, it should be appreciated that the analysis and HLA prediction need not be limited to a particular HLA-types, but that all HLA-types and allelic variants are contemplated herein, including HLA-E, HLA-F, HLA-G, HLA-H, HLA-J, HLA-K, HLA-L, HLA-V, HLA-DQA1, HLA-DMA, HLA-DMB, HLA-DOA, HLA-DOB, HLA-DPA1, HLA-DPB1, HLA-DRA, HLA-DRB345, HLA-MICA, HLA-MICB, HLA-TAP1, HLA-TAP2, and even newly discovered HLA types and their corresponding alleles. Moreover, it should be appreciated that the analysis need not be limited to a single HLA-type, but that multiple HLA-types are suitable for use herein. Consequently, the reference sequence may include two, three, four, or more HLA-types, with a collection of alleles for the respective HLA-types. As each HLA-type has a significant number of alleles, it is contemplated that not all of the known alleles need to be included in the reference sequence. For example, the reference sequence may include alleles with an allele frequency above a particular threshold such as an allele frequency of at least 0.1%, or at least 0.5%, or at least 1%, or at least 2%, or at least 5%. Therefore, and viewed from a different perspective, suitable reference sequences may include at least 10, or at least 30, or at least 50, or at least 100, or at least 200 or at least 500, or even more different alleles for at least one HLA type.

Similarly, it should be appreciated that the nature and type of the patient sequence reads may vary considerably. For example, contemplated patient sequence reads will include DNA and RNA sequences, each of which may be obtained using all methods known in the art. Moreover, such sequence reads may be provided from data storage (e.g., database) or from sequencing equipment. For example, DNA sequence reads may be derived from an NGS sequencing machine, and RNA sequences may be derived from rtPCR sequencing devices. Thus, the length of the patient sequence reads will typically be longer than 20 bases, more typically longer than 50 bases, and most typically be longer than 100 bases, however, generally shorter than 5,000 bases, or shorter than 3,000 bases, or shorter than 1,000 bases. Consequently, contemplated patient sequence reads may have a length of between 100 and 500 bases or between 150 and 1,000 bases.

To reduce computing time and data storage and/or memory requirement, it is further preferred that the patient sequence reads will be preselected to genomic areas where HLA-type genes are located. For example, patient sequence reads that map to chromosome 6p21.3 are especially contemplated. Likewise, the patient sequence reads may also be selected on the basis of one or more annotations that indicate likely position to a genome where HLA allele loci are known. Alternatively, the annotation may also directly reference the likelihood of the sequence as being an HLA allele.

Regardless of the length of the patient sequence reads, it is generally preferred that the patient sequence reads are decomposed in k-mers having a relatively short length, and particularly preferred lengths will typically be between 10 and 30. Notably, such short k-mer length allows for a higher resolution and accuracy in variant calling, particularly due to the weighted vote for a fragment containing such k-mers. Thus, k-mer length is typically between 10-30, or between 15-35, or between 20-40. Viewed from a different perspective, k-mers will preferably have a length of less than 60, even more preferably less than 50, and most preferably less than 40, but longer than 5, more typically longer than 8, and most typically longer than 10. For example, suitable k-mers will therefore have a length of between 5% and 15% of a length of the patient sequence read.

With respect to ranking and the composite match score, it should be noted that in most preferred aspects a match score will be generated on the basis of all k-mers that are present in the patient sequence reads, and that each voting (i.e., matching) k-mer has identical voting power. As a result, a patient sequence read will have a specific quantitative read support for each of the alleles in the reference sequence. Moreover, as in most instances each position in the genome has a >1 sequencing depth, and as each patient sequence read will only cover a fraction of the full length of an allele, each allele may receive multiple votes from multiple patient sequence reads. Most typically, all of the votes for an allele are added to so arrive at a composite match score for that allele. The composite match score for each of the alleles is then used for ranking and further analysis.

However, in alternative aspects of the inventive subject matter, it should be noted that the scoring and calculation of a composite score may also be modified to achieve one or more specific purposes. For example, a match score for a fragment need not be calculated from all of the matching k-mers, but may count only a random number or selection of k-mers. On the other hand, k-mers with less than a perfect match (e.g., 14/15 matching) may be given voting rights, possibly with a lower voting weight. Likewise, and particularly where metadata are available, voting weight may be reduced for k-mers and/or patient sequence reads where read quality falls below a specific threshold. On the other hand, where low sequencing depth is present, votes may be over-represented for a particular fragment. In yet another contemplated aspect, especially where read depth is relatively high (e.g., at least 15×, or at least 20×, or at least 30×), patient sequence reads for the same position may be eliminated or included based on the vote. Consequently, the composite match score may be based on all of the available votes, or only upon a fraction of the votes available for an allele.

While ranking typically relies on the cumulative match score, it should be recognized that ranking may also be corrected using at least one factor. Such correcting factors include fraction covered, sequencing depth, amount of unique k-mers, and metadata of the fragments as available. For example, voting weight may be reduced for alleles where coverage of the allele is below a predetermined threshold (e.g., less than 96%, or less than 94%, or less than 92%, etc.) and/or where sequencing depth is below a predetermined threshold (e.g., less than 15×, or less than 12×, or less than 10×, etc.). On the other hand, voting weight may also be increased, for example, for alleles where the percentage of unique k-mers is above a predetermined threshold (e.g., above 2%, or above 5%, or above 10%).

The top ranked allele is typically the first predicted allele for a given HLA-type, while the second ranked allele may be the second allele for the same HLA-type. It should be noted, however, that the scoring may be further improved or refined as needed, particularly where many of the ranks following the top rank have similar composite match scores. (e.g., where a significant portion of their score comes from a highly shared set of k-mers). In one preferred example, a score refinement procedure may be implemented that includes a recalculation in which the weight of k-mers that matched (either perfectly, or with a similarity of at least 90%, or at least 95%, or at least 97%, or at least 99%) the top-ranking k-mer are reduced by a correction factor. Such correction factor can devalue a vote by any predetermined amount. Most typically the correction factor will devalue the vote by 10%, or 20-40%, or 40-60%, or even more. This has the effect of reducing the weighted votes for genotypes that are similar to the top-ranking allele, relatively making the genotypes that differ more important. Thus, it should be noted that the first allele is identified based on the highest most support from all sequencing data, while the second allele is identified in a more heuristics based approach, using both the raw weighted vote, scaled weighted vote, and the coverage to determine if the second allele has support in the datasets (e.g., high scaled weighted vote and genotype coverage) or if the genome is homozygous for the first genotype (e.g., high raw weighted vote, very low scaled weighted vote, no other alleles with decent coverage). Viewed from a different perspective, re-ranking advantageously allows more accurate differentiation of the second allele even in the presence of alleles similar to the top ranking allele. Moreover, such method also allows ready identification of homozygous HLA-types. In addition, it should be appreciated that such methods do not require the use of a hash table and allow identification of the proper HLA allele without assembling the sequence reads into the HLA type. Still further, contemplated systems and methods also allow for use of DNA and/or RNA data.

Consequently, it should be appreciated that the methods and systems described above are particularly suitable for large scale HLA determination from various omics data, where omics data are present or available for analysis exceed 100 individuals, or exceed 200 individuals, or exceed 500 individuals, or exceed 1,000 individuals, or exceed 5,000 individuals, or exceed 10,000 individuals, or even more. Upon conclusion of the analysis, the HLA type of each individual is stored in a HLA database, which can be accessed by multiple parties, including the parties that provided or made available the omics data, and a third party that is interested in finding an HLA compatible or identical record or individual. Such HLA compatible or identical record or individual may be used for various purposes. Primarily, HLA matches will be useful for cell or organ transplantation, but also for determination of family relations, determination for ethnicity, determination of identity of a blood or tissue sample (e.g., in forensic use), etc.

Example

To validate HLA prediction, three independent known patient records and samples were obtained from the 1000 Genome project (NA19238, NA19239, and NA19240) and HLA-types were then predicted as discussed above. Remarkably and unexpectedly, HLA determination and prediction using De Bruijn graph method as described above had near perfect matches with the exception for HLA-C (for NA19238), DRB1 (for NA19239), and HLA-C (for NA19240) as can be seen in FIG. 1. Notably, the three discrepancies can be explained as incorrect data in the published record. The HLA prediction method presented here has demonstrated 100% accuracy across a diverse panel of 5 HLAs in 3 individual datasets. According to the data, there is no support for "Published" C*18:01, while there is substantial support for the Predicted C*18:02. Furthermore, Mendelian inheritance dictates the "Published" DRB1*13: 01 on both alleles is impossible (given that NA19238 and NA19239 are parents of NA19240).

In still further experiments, the inventor predicted HLA-A, HLA-B, HLA-C, HLA-DRB, and HLA-DBQ haplotypes for 20 actual patient samples and validated the predicted HLA type in a contracting lab using sequence-specific oligonucleotide (SSO) and sequence-specific primer (SSP) methods. As can be taken from FIG. 2, the prediction accuracy across all 20 patient samples was 100%. Likewise, a further 40 patients were analyzed and predicted HLA types were validated using long range sequencing (PacBio SMRT sequencing). Notably, as can be seen from FIGS. 3 and 4, only 4 predictions were discordant, while 7 predictions were indeterminate due to inability to determine the sequence. The remaining 97.4% of all data were concordant with the predicted HLA type.

As will be readily appreciated, predicted HLA types can be stored in a database and can represent either donor HLA types, and especially bone marrow donors, stem cell donors, cord blood donors, etc., and/or transplant recipients such as patients that await heart, liver, lung, kidney, skin, or pancreas transplant.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously. Moreover, groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A tissue matching engine, comprising:

an HLA database storing HLA information for a donor tissue including a top ranked HLA allele as a donor first HLA-type and a re-ranked non-top HLA allele as a donor second HLA type;

at least one computer readable memory storing software instructions; and at least one processor coupled with the HLA database and the memory, and upon execution of the software instruction then performs the operations of:

obtaining omics data from a recipient tissue of a patient;

decomposing the omics data into k-mers having a length less than 60;

generating a composite de Bruijn graph from the k-mers and from a reference sequence for known HLA alleles;

ranking the known HLA alleles based on a composite match score from votes of sequence reads in the omics data where the votes are from k-mers matching the known HLA alleles;

identifying a recipient first HLA type of the recipient tissue from a top ranked HLA allele of the known HLA alleles;

identifying a recipient second HLA type of the recipient tissue from a re-ranked non-top-ranking HLA allele of the known HLA alleles based on an adjusted composite match score;

identifying, from the HLA database, the donor tissue as being compatible with the patient based on the recipient first HLA type and the donor first HLA type or the recipient second HLA type and the donor second HLA type; and wherein the omics data is derived from at least one of the following: RNAseq data, whole genome sequencing, exome sequencing, transcriptome sequencing, and targeted sequencing.

2. The tissue matching engine of claim 1, wherein the recipient first or second HLA types match is determined to a depth of at least four digits.

3. The tissue matching engine of claim 2, wherein the match is determined to a depth of at least six digits.

4. The tissue matching engine of claim 1, wherein the recipient first or second HLA types include one or more of the following: an HLA-A type, an HLA-B type, an HLA-C type, and HLA-DRB-1 type, and an HLA-DQB-1 type.

5. The tissue matching engine of claim 1, wherein the recipient first and/or second HLA type is identified to a depth of at least 4 digits.

6. The tissue matching engine of claim 1, wherein the omics data comprises partial omics data, and wherein the partial omics data comprises data from one chromosome.

7. The tissue matching engine of claim 6, wherein the data from one chromosome represent chromosome 6p21.3.

8. The tissue matching engine of claim 1, wherein the known HLA alleles represent at least 26 HLA types.

9. The tissue matching engine of claim 1, wherein the donor tissue comprises a banked tissue.

10. The tissue matching engine of claim 9, wherein the banked tissue includes at least one of the following: cord blood and an organ.

11. The tissue matching engine of claim 1, wherein the recipient tissue comprises a solid organ.

12. The tissue matching engine of claim 11, wherein the solid organ comprises at least one of the following: a lung, a liver, a heart, or skin.

13. The tissue matching engine of claim 1, wherein the recipient tissue comprises at least one of the following: bone marrow, blood, and a tumor.

14. The tissue matching engine of claim 1, wherein the donor tissue comprises stem cells.

15. The tissue matching engine of claim 13, wherein the stem cells comprise bone marrow stem cells.

16. The tissue matching engine of claim 1, wherein the k-mers have length less than 50.

17. The tissue matching engine of claim 1, wherein the k-mers have a length between 10 and 30.

18. The tissue matching engine of claim 1, wherein the adjusted composite match score is adjusted using depth of coverage.

* * * * *